(12) United States Patent
Rastoutsau et al.

(10) Patent No.: US 11,955,242 B2
(45) Date of Patent: Apr. 9, 2024

(54) METHOD FOR AUTOMATIC DIAGNOSIS OF CONDITIONS OF AN OBJECT AND A SYSTEM FOR IMPLEMENTING THE SAME

(71) Applicants: Uladzimir Rastoutsau, Minsk (BY); Aliaksandr Lukyanau, Minsk (BY); Kanstantsin Lukyanau, Minsk (BY); Roman Gromov, Minsk (BY); Sergey Vinogradov, Minsk (BY)

(72) Inventors: Uladzimir Rastoutsau, Minsk (BY); Aliaksandr Lukyanau, Minsk (BY); Kanstantsin Lukyanau, Minsk (BY); Roman Gromov, Minsk (BY); Sergey Vinogradov, Minsk (BY)

(73) Assignees: Uladzimir Rastoutau, Minsk (BY); Aliaksandr LUKYANAU Lukyanau, Minsk (BY); Kanstantsin Lukyanau, Minsk (BY); Sergey Vinogradov, Minsk (BY)

( * ) Notice: Subject to any disclaimer, the term of this patent is extended or adjusted under 35 U.S.C. 154(b) by 635 days.

(21) Appl. No.: 16/641,452

(22) PCT Filed: Dec. 28, 2017

(86) PCT No.: PCT/IB2017/058446
§ 371 (c)(1),
(2) Date: Feb. 24, 2020

(87) PCT Pub. No.: WO2019/038581
PCT Pub. Date: Feb. 28, 2019

(65) Prior Publication Data
US 2021/0142909 A1    May 13, 2021

(30) Foreign Application Priority Data
Aug. 24, 2017   (BY) .................. a20170315

(51) Int. Cl.
*G16H 50/30* (2018.01)
*A61B 5/00* (2006.01)
*G16H 50/20* (2018.01)

(52) U.S. Cl.
CPC ........... *G16H 50/30* (2018.01); *A61B 5/0002* (2013.01); *A61B 5/4842* (2013.01);
(Continued)

(58) Field of Classification Search
CPC ........ G16H 50/30; G16H 50/20; G16H 50/70; A61B 5/0002; A61B 5/4842;
(Continued)

(56) References Cited

U.S. PATENT DOCUMENTS

2010/0042011 A1* 2/2010 Doidge ................. G06T 17/10
600/544

FOREIGN PATENT DOCUMENTS

WO   WO-2016176117 A1 * 11/2016 ......... A61B 5/02007

OTHER PUBLICATIONS

Kitchen, Christina M R; Yeghiazarian, Lilit; Hoh, Rebecca; McCune, Joseph M; Sinclair, Elizabeth; et al. "Immune Activation, Cd4+ T Cell Counts, and Viremia Exhibit Oscillatory Patterns over Time in Patients with Highly Resistant HIV Infection." PLoS One 6.6: e21190. Public Library of Science. (Year: 2011).*

(Continued)

*Primary Examiner* — Linh Giang Le

(57) ABSTRACT

This invention relates to automatic medical diagnostic methods and systems. The object of the invention is to provide a method and a system of passive and fully automated nosological diagnostics. The objective is solved based on the method of the spectral-dynamic analysis of a wave signal from the body surface, recognition and assessment of the degree of matching to nosological groups of spectral-dynamic samples to determine the presence or stages of a (Continued)

disease. The system is made as a distributed system with multiple terminals for recording wave signals and provided with a system for transmitting them to the center for processing and establishing a diagnosis. To achieve more accurate diagnostic, a resonance and compensation biological feedback is used depending on the energetic type of active samples.

11 Claims, 3 Drawing Sheets

(52) U.S. Cl.
CPC .......... *A61B 5/7225* (2013.01); *A61B 5/7275* (2013.01); *G16H 50/20* (2018.01)

(58) Field of Classification Search
CPC ....... A61B 5/7225; A61B 5/7275; A61B 5/05; A61B 5/00; A61B 5/7221; A61B 5/7235; A61B 5/7264
See application file for complete search history.

(56) References Cited

OTHER PUBLICATIONS

Rostovtsev V.N. et al., New technology of physical medicine, (Nov. 24, 2009), URL: http://www.kmsd.su/vracham/nauchnye-stati/ novaya -tekhnologi ya - fizicheskoy- meditsiny-rostovtsev-v-n- ulashchik-v-s.

Rostovtsev V.N., New wave diagnostics technology, (Apr. 11, 2013), URL: http://www.kmsd.su/vracham/nauchnye-stati/novaya- tekhnologiya- volnovoy-diagnostiki-rostovtsev-v-n.

* cited by examiner

METHOD FOR AUTOMATIC DIAGNOSIS OF CONDITIONS OF AN OBJECT AND A SYSTEM FOR IMPLEMENTING THE SAME

This invention relates to medical diagnostic methods and systems, more specifically, to the automatic disease diagnostic systems. The invention may also be used to diagnose conditions of any biological objects.

Conventional automated diagnostic systems and methods are actually limited to two types, as follows:

Information auxiliary systems and databases of diseases and signs thereof. Such systems help physicians establish diagnosis by combining computer-based techniques and analysis of already manifested external signs and symptoms.

Measuring and visualizing systems and methods (for example, cardiograms, tomography, etc.) allowing earlier manifested structural changes to be definitely detected. In such cases, the automation mainly facilitates finding and detecting structural changes.

Combining these methods improves accuracy of detecting a disease, however, it cannot identify the risk disease occurrence at early stages, and as regards structural changes, it provides only a part of the information about the status, and in any case it requires involvement of a physician to make a diagnostic decision. In other words, in this case it refers not to the automated diagnostics, but to a partial automation of the diagnostic process.

The most commonly used diagnostics is the so-called automated diagnostics of cardiovascular diseases based on recording and analysis of cardiograms followed by recognition of specific features thereof, including waves, peaks (teeth), complexes and boundaries thereof in order to make evaluative decisions by comparing them with reference cardiogram database. Comparison of different cardiogram processing algorithms is provided in the work of Petrov S. P., Epishina E. V. and Voronin V. V. "Evaluation of Pattern Recognition Algorithms for Solving Problems of Automated Electrocardiogram Analysis" [Eurasian Union of Scientists (EUS) #VIII, 2014\Technical Sciences, pp. 27-29].

Actually, the object of the automated ECG diagnosis is to assess the myocardium functional state, and not nosological status of the cardiovascular system, i.e. specific diseases related to the functioning of this system. In other words, in any case, establishing diagnosis requires the physician's interpretation, i.e. it is not fully automated and is subject to bias. Such a system and those similar thereto are designed only to facilitate the diagnosing the diseases or conditions and allow only already manifested diseases or conditions to be diagnosed. This is characteristic of actually all existing methods of medical diagnostic automation.

Existing automated diagnostic systems, for example, "An Automated Personal Medical Diagnostic System, Method and Arrangement" WO 2013066642, are mainly based on the following sequential scheme:

a measuring (diagnostic) device of different levels of complexity based on specific biophysical effect;
an analog-to-digital converter (ADC);
a computer or a dedicated processor;
a database;
a control unit;
a user terminal.

Some of these systems are also used for the remote diagnostics. In this case, a user should be actually provided with, at least, a diagnostic unit or a sensor, an ADC and a transmission device. As a rule, however, the diagnostic unit itself is a rather complicated device and delivering it to and training a patient how to use it require involvement of other persons.

The basis for solving the problem of the automated nosological diagnostics is the functional spectral-dynamic diagnostics being a practical implementation of the method in the medical field subject to Eurasian Patent for "The Method of Detecting and Testing Subprocesses in a Complex Wave Field of an Object", No. 017369 with the priority on 4 May 2011.

Functional spectral-dynamic diagnostics are performed by converting an electromagnetic wave signal from a surface of a patient's body into spectral-dynamic images of processes occurring in the patient's organism and recognizing spectral-dynamic images of reference markers of pathological and other processes in the complex wave field of the patient's organism. Recognition of every marker is characterized by the level of overall matching, level of pathological matches and level of the process relevance. These characteristics help assess diagnostic significance of every marker and also form a disease diagnostic image, more specifically images of different stages of the disease progress, including the risk stage, latent stage, early (first manifestations) stage and manifest (late) stage by using a set of markers belonging to a selected body organ-tissue or functional system.

The main disadvantage of the conventional method is labor intensity of the diagnosis process, and also the presence of a bias and the requirement for high professional skills of a diagnostician involved in assessing a set of indicators and inability to perform the diagnostics. In addition, complex processing processes require the computer equipment intensive resources which also confine the use of the method.

The object of the invention is to provide a fully automated nosological diagnostics, i.e. diagnostics:

(1) of different specific diseases (in all organism systems)
(2) at main stages of progress thereof, including stages of actual risk, latent (hidden) progress and clear manifestation,
(3) technologically readily accessible for a wide range of patients and medical workers.

The object of the invention is also to provide an automated nosological diagnostic system suitable to diagnose a wide range of diseases and processes being characteristic of different body systems and, furthermore, to promote effectiveness and widen the area of usage to cover remote patients.

The objects set are to be solved by using improvements described in this application.

According to the invention, the method for automatic diagnosis of conditions of an object comprises, like in the prior art, the recording of signals from the object's surface, signal processing, comparing with references and performing diagnostic operations. The method is characterized in that an electromagnetic wave signal is recorded, the signal is processed by performing the spectral-dynamic analysis and spectral-dynamic matching of the processed signal is determined to, at least, one wavelength sample being a reference of the object's status to be diagnosed.

According to the invention, when the degree of matching below the predetermined value for the nosology to be diagnosed is established, a decision is made and the absence of the status being diagnosed is indicated, and when the degree of matching equals or exceeds the predetermined level, the matching of the processed signal is determined to, at least, one more wavelength sample, being the reference of the same status, and when the degree of matching is established below the next predetermined value for the nosology to be diagnosed, a conclusion is made and the risk of the onset of the status to be diagnosed is indicated, and when the degree of matching being equals to or exceeds the predetermined value, the matching of the processed signal is determined to, at least, one more next wavelength sample, being referential to the same status, and when the degree of matching is established below the next predetermined value, a decision is made and the presence of the latent phase of the status progress is indicated, and when the degree of matching being equal to or higher this predetermined value is established, a decision is made and the manifested phase of the status to be diagnosed is indicated.

Therefore, conditions with regard to which reference groups of wavelength samples are formed are automatically diagnosed.

Further improvement resides in the fact that the spectral-dynamic matchings of the processed signal are determined using a predetermined group of wavelength samples, being referential to the object's nosological status to be diagnosed, and the degree of matching thereof is determined by weighted averaging matching degrees of each sample of the group, i.e. accounting the weight of the sample set for the given group.

A further improvement is that sets of samples for a series of conditions are preliminary created, a degree of matching of the recorded processed signal is assessed with respect to each of them, at least one most relevant status with the highest matching degree is automatically selected and automated diagnosis is performed therefor according to the reference group of samples.

In fact, groups of reference samples from a database are formed based on clinical studies for each nosology to be diagnosed, and also critical values of degrees of matching thereof to specific phases of progress of nosological conditions are determined.

To more reliably assess the degree of matching, an operation of the mathematical-and-statistical procedure for variance estimation is used in addition to logical comparison procedures, and corrections for the data variation are introduced in matching values.

In one of the embodiments, a sequential set of electromagnetic wave signals is recorded, signals are processed using the spectral-dynamic analysis and diagnostic operations are performed to include as follows: determining the spectral-dynamic matchings of the processed signal with, at least, one wavelength sample being a reference for the object's status to be diagnosed, averaging the obtained degrees of matchings of each record and then using the averaged degree of matching to the sample for the entire set.

In the alternative embodiment, a sequential set of intervals is sampled from the total duration of the record of a wave electromagnetic signal, the signal interval samples are processed using the spectral-dynamic analysis and diagnostic operations are performed to include as follows: determining the spectral-dynamic matchings of the processed interval of the recorded signal to, at least, one wavelength sample being a reference for the object's status to be diagnosed, averaging the obtained degrees of matching and then using the averaged degree of matching to the sample.

The improved method additionally provides diagnostic testing by forming a wave signal of the recognized sample and applying this signal to the object's surface using a test electrode with this sample, provided that it is related to a hyperergetic type, being inverted, converted to the analogue form, amplified, fed to an additional testing electrode located on the object's surface and the testing effect is produced, then the relevance of the status being diagnosed is determined either by the rate or biofeedback response time. A criterion for starting the diagnostic testing is availability of the matching degree value of the sample satisfying a minimax status specified on other samples of the group. A twofold difference in degrees of matching of two predetermined samples may serve as an example of the minimax status.

Hyperergetic processes are characterized, as a rule, by active, for example, inflammatory processes, and in this case, when an inverted signal is supplied, the occurring process is compensated and the degree of the organism responsiveness allows the disease stage and severity to be assessed.

Upon occurrence of hypoergetic processes, respective processes are inhibited and an amplified sample wave signal can stimulate an organism or a system thereof to normal functioning.

In this case, the biological feedback is provided by periodically repeating a diagnostic procedure and observing changes in degrees of matching of wave signals to be diagnosed and tested.

It is preferable that an additional diagnostic testing is sequentially performed with respect to all samples satisfying to minimax conditions thereof.

To practically implement the claimed technology, an automatic diagnostic system for diagnosing object's conditions is provided comprising a diagnostic electrode connected in series with a broad-band amplifier, an analog-to-digital converter, a signal processing unit and a comparator-recognizer containing samples from the database.

In the system claimed, the diagnostic electrode is configured to record an electromagnetic wave signal from the object's surface. The electrode shape may depend on the shape of an object being examined. As a rule, a plane-type electrode is used in medical diagnostics.

The signal processing unit is made in the form of a spectral-dynamic analyzer, the comparator-recognizer is made in the form of a module for recognizing images of predetermined samples in the spectral-dynamic representation of an input signal, with the second comparator input being linked with the buffer database of samples relevant to the status to be diagnosed and singled out from the total sample database, while a positive comparator output is linked with the predetermined sample matching degree assessment unit the output of which is linked with the decision-making unit connected to the control unit and buffer database, and the control unit is connected to the matching degree assessment unit, database and control terminal. The control terminal is designed to select a diagnostic problem, i.e. to select the predetermined group of samples, control the process and indicate the obtained diagnosis.

This system is designed to automatically diagnose predetermined nosological conditions and identify actual risks and stages of progress of these statuses.

In the improved system, the series-connected diagnostic electrode, broad-band amplifier and analog-to-digital converter are connected to a transmission device to form a remote user terminal connected via a transmission medium to a multichannel receiver-switching device and via it to a base spectral-dynamic analyzer.

An expanded system comprises multiple user terminals and transmission media, including Internet, mobile, satellite and cable communications systems.

In this configuration, a rather simple user terminal combined with any communication facilities allow for implementing a multiuser system and extend a range of diagnostic system users to cover the population of a country or the entire planet. In this case, a set of features of a rather simple passive device for receiving an electromagnetic wave signal followed by conversion thereof into a digital form combined with spectral-dynamic signal processing, recognition of images of selected nosological groups of markers in the converted wave signal, determination of degrees of matching to nosological groups of markers and comprehensive matching thereof to the specified criteria—all this provides a new technical result—automatic identification of risk, availability and a stage of the selected nosology for a wide range of users.

A broad-band amplifier and an ADC may be made on sample integrated circuits or on a single chip and connected to any communication device, for example, via a USB port.

Under the specific recording mode and rather substantial broad-bandness of a sound-recording device of a mobile phone, a diagnostic electrode may be connected directly to a microphone input thereof.

In this case, low cost and accessibility to a remote terminal device in combination with a centralized wave signal processing in a digital format and automatic recognition, determination of the degree of matching and common databases of samples provide on-line automation of the nosological diagnostics.

To perform additional testing, the system additionally comprises a database of test samples linked with a buffer database and a modulator inverting the sample depending on the type thereof, with the modulator control input being connected to the control unit and the modulator output being connected in series to the digital-to-analog converter, amplifier and test electrode located on the object surface.

This system provides enhanced testing validity by establishing a biological feedback and additionally examining response of the object under study.

Figure 1:
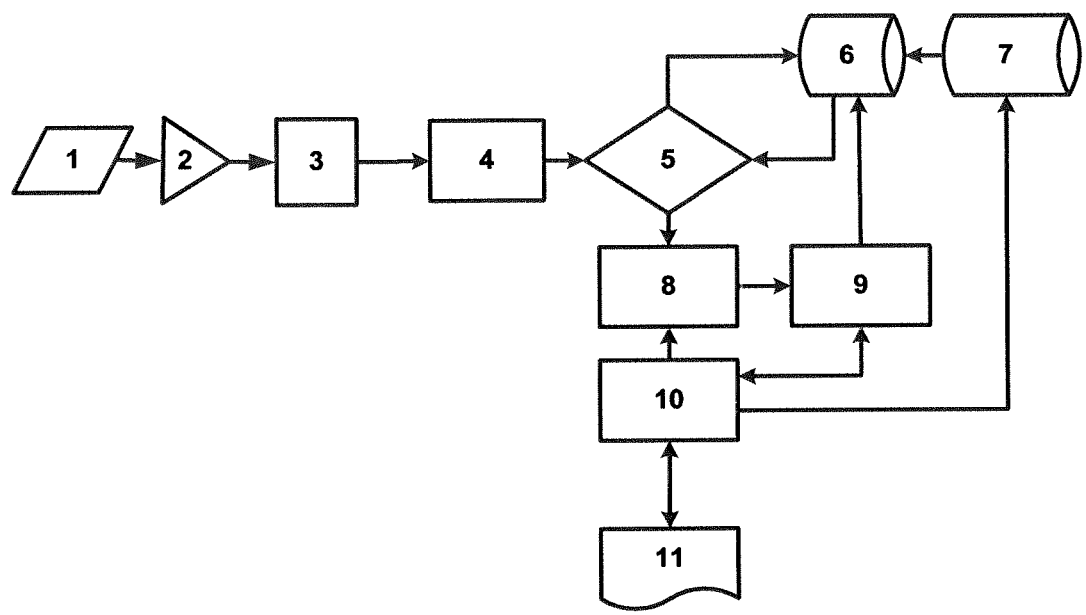
FIG. 1 illustrates a basic scheme of the automated diagnostic system embodied to implement the provided method.

A specific embodiment of the automated diagnostic system according to the invention illustrated in FIG. 1 comprises a diagnostic electrode DE (1) which is connected in series to a broad-band amplifier BBA (2), an analog-to-digital converter ADC (3) and a signal processing unit configured as a spectral-dynamic analyzer SDA (4). The SDA output is connected to a comparator-recognizer CR (5) configured as a recognizer of images of predetermined samples in the spectral-dynamic representation of an output signal, with the second comparator input being connected with an output of a reference marker buffer database RMBD (6) being relevant to the nosological status to be diagnosed and singled out from the common marker database MD (7). A positive output of the comparator-recognizer CR (5) is connected to the predetermined sample matching degree assessment unit MAU (8) the output of which is linked with a decision-making unit DMU (9) connected to the control unit PCU (10) and a buffer database RMBD (6), and the control unit PCU (10) is linked with the matching degree assessment unit MAU (8), database MD (7) and a control terminal TERM (11) used to select the predetermined group of samples, control the process and indicate the obtained diagnosis.

The system operates as described hereinafter. An electromagnetic wave signal of the object is received by a diagnostic electrode DE (1) configured in this case as a plate antenna-electrode having approximate dimensions of 40×75 mm and made of a conductive material allowed for use in medicine to contact with the body surface. In this case, it is made of food grade stainless steel. A passively received signal is amplified by the broad-band amplifier (2) in the frequency range of 10 Hz-20 kHz and is digitized by the ADC (3) in 5 intervals 3 seconds each for 35 seconds.

The spectral-dynamic analyzer SDA (4) performs rapid wavelet transforms of digital signals. A series of transformations results in the images of wave processes taking place in a human body, organs, systems, cells thereof and in other biological objects present in the body. These images are supplied to the comparator-recognizer CR (5) in which the images similar to images of reference markers in the predetermined nosological group stored in the buffer database RMBD (6) and fed to the second comparison input are recognized.

The spectral-dynamic matchings of the processed signal to a group of wavelength samples being a reference for the object's status to be diagnosed is determined in the comparator-recognizer CR (5), and the degree of matching thereof is determined in the MAU (8) by (weighted) averaging degrees of matching of each sample of the group with consideration for the weight thereof set for the given group.

In this case, it should be accounted that groups of samples, weights of samples in the group and matching criteria are set for each specific nosology based on clinical tests (trials).

The matching assessment value is supplied to the decision-making unit DMU (9) in which a diagnostic decision regarding the absence of disease is taken subject to the criteria set or regarding further assessment with the next sample in the group stored in the buffer database RMBD (6). In the latter case, the comparison-recognition-matching degree assessment cycle is repeated for the next sample in the group. When the cycles for all samples of the group are progressed, the degree of matching is comprehensively assessed and the final diagnostic decision is made.

Upon making the decision regarding the predetermined nosology and receipt of the decision code at the control terminal TERM (11), the control unit PCU (10) starts checking the next nosology based on the set program or the terminal command.

In this case, the control unit PCU (10) issues a command to load the next nosological group of reference markers into the reference marker buffer database RMBD (6).

In case the comparator-recognizer CR (5) produces no results of matching based on the predetermined reference markers, a command to issue the next reference marker in the group is fed from the second CR (5) output to reference marker buffer database RMBD (6).

The control unit PCU (10) controls and synchronizes operation of all system elements and also exchange of commands with the control terminal and also transmits a command to the terminal TERM (11) to indicate a diagnostic decision.

Therefore, the described system allows nosological risks and disease stages to be automatically identified.

Figure 2:
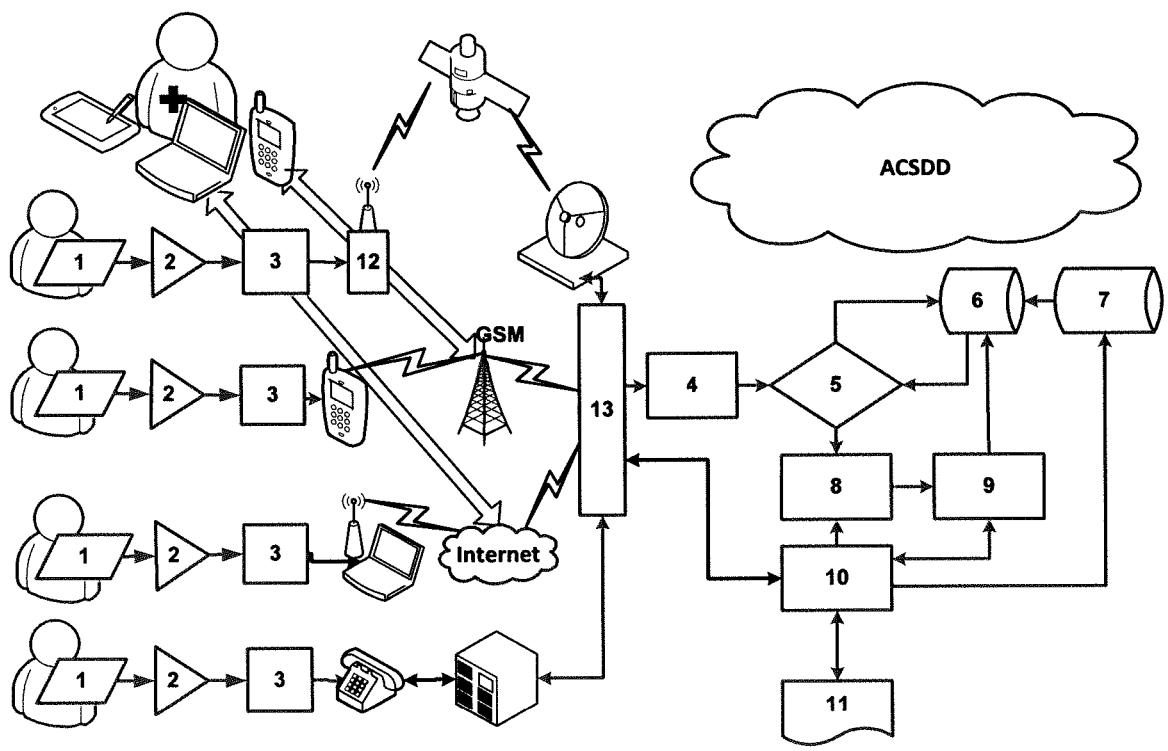
FIG. 2 illustrates a scheme of the automated diagnostic system improved for the accessible remote use with application of different communication means.

One more embodiment of the multiuser automated diagnostic system according to this invention illustrated in FIG. 2 comprises the following components as described hereinafter.

Multiple user terminals each of which comprises a diagnostic electrode DE (1) which is connected in series with the broad-band amplifier BBA (2) and the analog-to-digital converter ADC (3).

The ADC (3) digital output is connected to the digital communication device (12), which may be configured and used as, for example, a mobile GSM or satellite phone, a computer with connectivity to Internet or a digital landline phone, etc. These communication devices are connectable via communication channels thereof to a multiplexer MP (13) of the automatic center for spectral-dynamic diagnostics (ACSDD). This center may be configured as a separate server equipped with communication means or based on a cloud technology.

The multiplexer MP (13) receives wave signals recorded in a digital form from different remote terminals and supplies them to the spectral-dynamic analyzer SDA (4) input. The SDA output is connected to the comparator CR (5) configured as is made in the form of a module for recognizing images of predetermined samples in the spectral-dynamic representation of an input signal, with the second comparator input being linked with the buffer database RMBD (6) of reference markers being relevant to the nosological status to be diagnosed and singled out from the common marker database MD (7). A positive comparator-recognizer CR (5) output is linked with the predetermined sample matching degree assessment unit MAU (8) the output of which is linked with the decision-making unit DMU (9) connected to the control unit PCU (10) and buffer database RMBD (6), and the control unit PCU (10) is connected to the matching degree assessment unit MAU (8), database MD (7), multiplexer MP (13) and control terminal TERM (11) to select the predetermined group of samples, control the process and indicate the obtained diagnosis.

The system operates as described hereinafter. An electromagnetic wave signal of the object is received by a diagnostic electrode DE (1) configured in this case as a plate antenna-electrode made of a conductive material allowed for use in medicine to contact with the body surface. A passively received signal is amplified by the broad-band amplifier BBA (2) in the frequency range of 10 Hz-20 kHz and is digitized by the ADC (3) in 5 intervals 3 seconds each for 35 seconds. The ADC (3) output is connected to the communication device (12), for example, to a mobile phone which communicates with a multiplexer MP (13) of the ACSDD either via the GSM, or via WiFi, or via Bluetooth channel. The communication device (12) transmits the patient's identification data simultaneously with the recorded signal.

Figure 5:
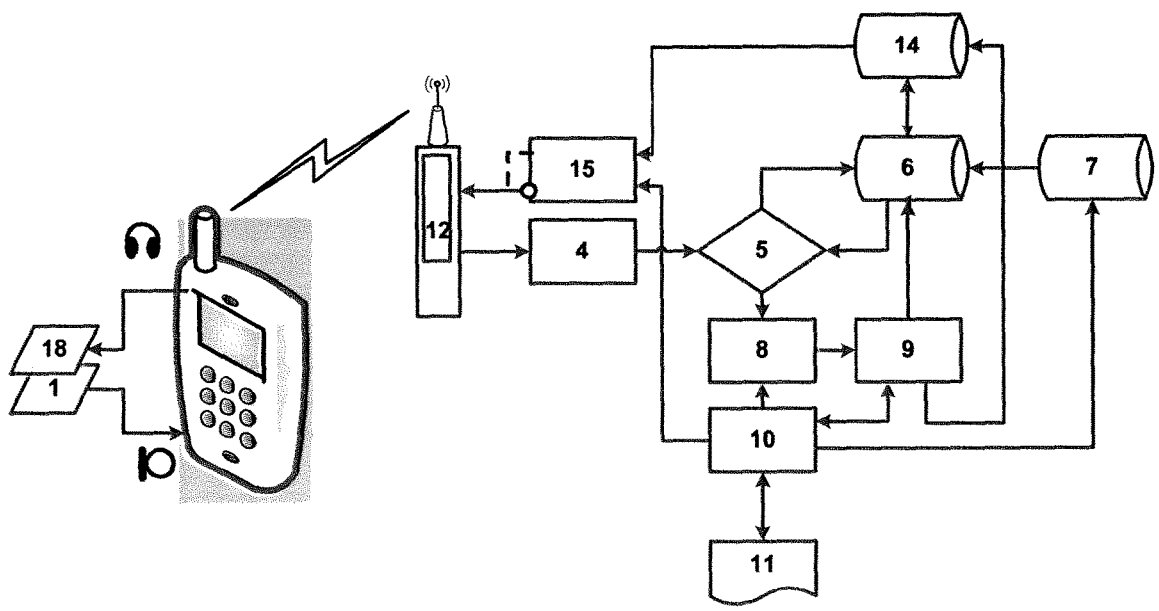
FIG. 5 illustrates a simplified scheme of the automated diagnostic system with the use of additional testing and biological feedback for the remote user with application of a mobile phone and an audio system thereof.

In one of the embodiments (shown in FIG. 5), the mobile phone amplifier and ADC of the audio channel may perform functions of the amplifier (2) and ADC (3) in the remote terminal, and the diagnostic electrode (1) is connected to the microphone input in the recording mode. In this case the application for the Android OS or iOS may perform functions of the controller of this remote terminal.

As a result of a series of transformations in the spectral-dynamic analyzer SDA (4), images of wave processes occurring in the human body, organs, systems, cells thereof and in other biological objects present in the body are formed. These images are supplied to the comparator-recognizer CR (5) in which the images similar to images of reference markers in the predetermined nosological group stored in the buffer database RMBD (6) and fed to the second comparison input are recognized.

The spectral-dynamic matchings of the processed signal to a group of wavelength samples being a reference for the object's status to be diagnosed is determined in the comparator-recognizer CR (5), and the degree of matching thereof is determined in the MAU (8) by (weighted) averaging degrees of matching of each sample of the group with consideration for the weight thereof set for the given group.

In this case, it should be accounted that groups of samples, weights thereof in the group and matching criteria are set for each specific nosology based on clinical tests (trials).

The matching assessment value is supplied to the decision-making unit DMU (9) in which a diagnostic decision regarding the absence of disease is taken subject to the criteria set or regarding further assessment with the next sample in the group stored in the buffer database RMBD (6). In the latter case, the comparison-recognition-matching degree assessment cycle is repeated for the next sample in the group. When the cycles for all samples of the group are progressed, the degree of matching is comprehensively assessed and the final diagnostic decision is made.

In case the comparator-recognizer CR (5) produces no matching results based on the predetermined reference marker, a command to issue the next reference marker in the group is fed from the second CR (5) output to reference marker buffer database RMBD (6).

Upon making the decision regarding the predetermined nosology and receipt of the decision code at the control terminal TERM (11), the control unit PCU (10) transmits the decision to the multiplexer MP (13) and further via a communication channel to a respective user and/or via Internet or mobile communication to a consulting physician or a respective Medical Center in which a patient is followed up.

Then, upon request from a user, the control unit PCU (10) starts checking the next nosology or next patient based on the set program or the terminal command or via MP (13).

In this case, the control unit PCU (10) issues a command to load a respective nosological group of reference markers into the reference marker buffer database RMBD (6).

The control unit PCU (10) controls and synchronizes operation of all system elements and also exchange of commands with the control terminal and also transmits a command to the terminal TERM (11) and/or to a patient's terminal to indicate a diagnostic decision.

In this configuration, the PCU (10) additionally communicates with patients receiving requests thereof and forwards diagnostic decisions received thereto.

This set of features of a simple passive receiving device configured to receive an electromagnetic wave signal and digitize it, a transmitter-receiver system in combination with the spectral-dynamic signal processing, recognition of images of selected nosological marker (samples) groups in the digitized wave signal, determination of the degrees of matching to nosological groups of markers and comprehensive matching thereof to the set criteria provides a new technical result—automatic risk identification, presence and stages of the selected nosology for a wide range of users with distributed resources.

Therefore, the described system allows nosological risks and disease stages to be identified in a multiuser automatic mode.

The concentration of main resources in one or multiple centers and a simple, accessible peripheral configuration allow for providing a distributed and extensive global diagnostic system characterized by high accuracy, low cost and great effectiveness.

Furthermore, any improvements, modifications and adjustments are performed in this system in a centralized manner and enter into force simultaneously for all users.

Figure 3:
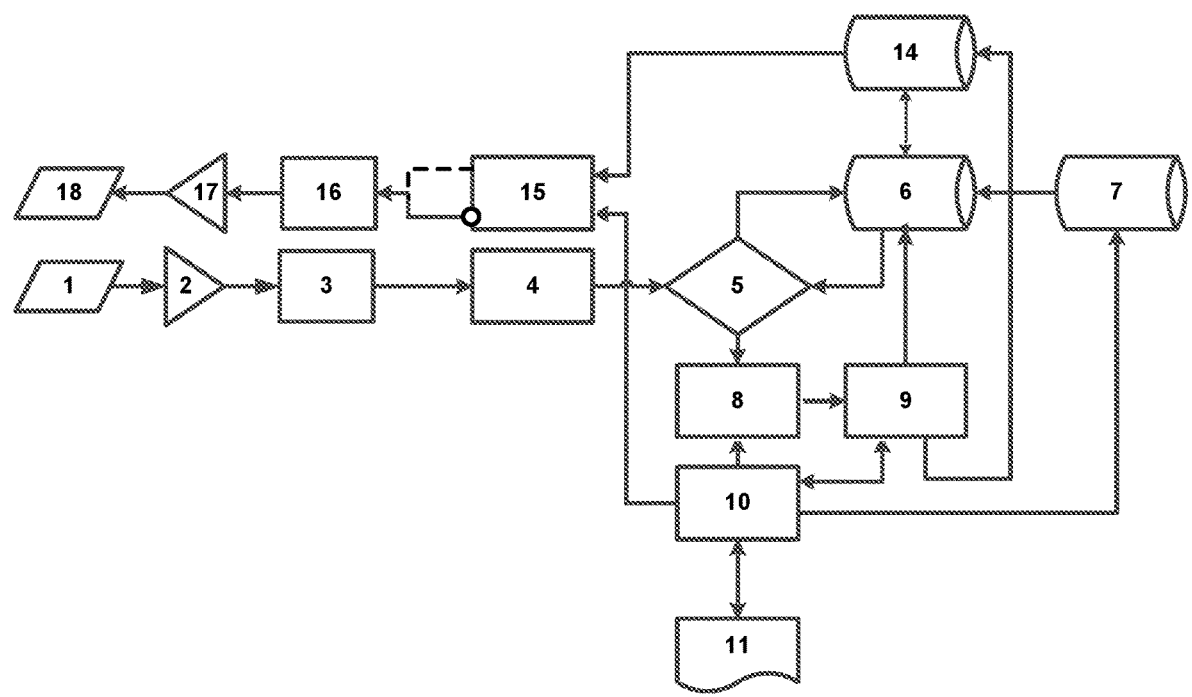
FIG. 3 illustrates an improved scheme of the automated diagnostic system with the use of additional testing and biological feedback.

One more specific embodiment of the automated diagnostic system according to the invention illustrated in FIG. 3 comprises an additional testing channel with a biological feedback.

In this embodiment, the scheme illustrated in FIG. 1 is provided with an additional testing marker database TMD (14) selected for testing. It is linked with the buffer reference marker database RMBD (7), the decision-making unit DMU and a test signal modulator TSM (15) to reversely convert the digital sample selected for testing into an analog wave signal. A direct or inverted signal is formed at the modulator output by a control signal supplied from the PCU (10) depending on the type of the process to which the sample is related. In case of the hyperergetic process, an inverted signal is used, while in hypoergetic process a forward signal is used. The signal formed by the modulator TSM (15) is supplied to the digital-to-analog converter DAC (16) input, is amplified by the broad-band amplifier TSBBA (17) and is fed to the testing electrode TE (18).

In one of the embodiments, an invertible converter ADC-DAC and an invertible amplifier may be used in the diagnostic and testing channels.

After such testing, a disease stage is additionally diagnosed based on compensation or stimulation results.

In this configuration, the system may be also used for treatment by compensating or stimulating spectral-dynamic parameters of pathological or other conditions and processes.

Figure 4:
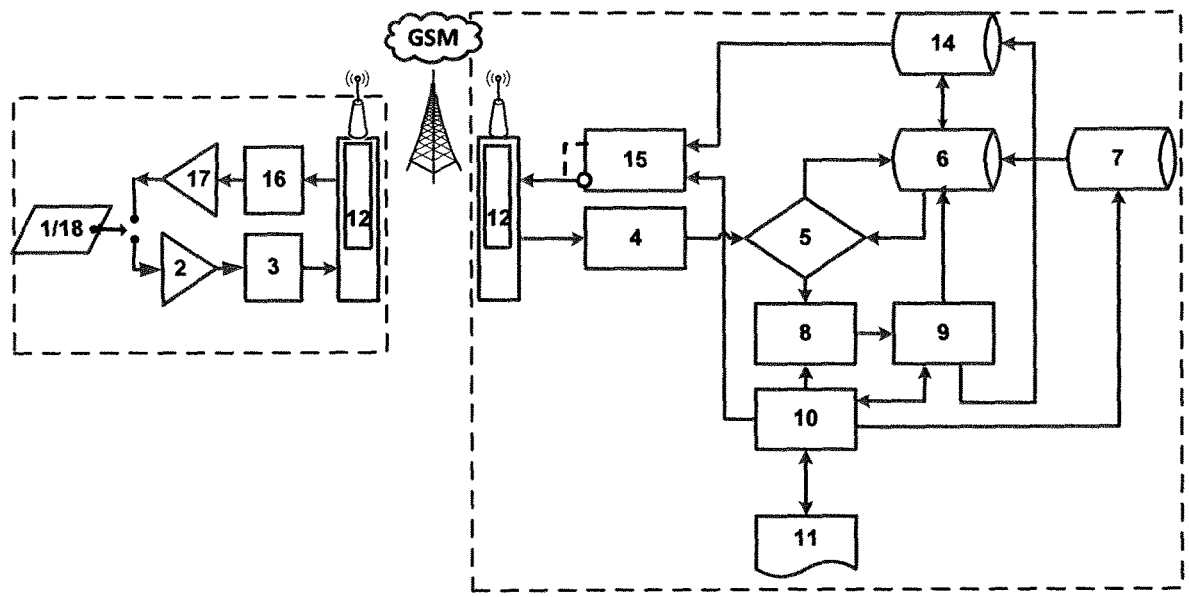
FIG. 4 illustrates an improved scheme of the automated diagnostic system with the use of additional testing and biological feedback for the remote user.

FIG. 4 illustrates an improved scheme of the automated diagnostic system with the use of additional testing and biological feedback for a remote user. In this case, the scheme in FIG. 3 is supplemented with two communications units 12, one of which is connected to the ADC 3 output and DAC 15 input, while the second one is connected to the analyzer 4 input and the modulator 15 switchable output, with both communication units being integrated into the shared network and exchanging the data according to the preset protocol. Any mobile devices such as mobile phones, smartphones, tablets, notebooks, modems, access points, etc. may be used as communication devices 12. The GSM, WiFi, Bluetooth, NFC, IR networks and others may be used as the data transmission networks. In addition, functions of a diagnostic (1) and test (18) electrodes may be combined in one electrode by switching thereof in a mobile alternative embodiment for the ease of use.

FIG. 5A illustrates a more improved and simplified scheme of the automated diagnostic system with the use of additional testing and biological feedback for a remote user with application of a mobile phone and audio system thereof.

In this embodiment, available input and output audio channels of the external mobile phone headset having rather broad band and high sensitivity are proposed to be used as an amplifier 2, ADC 3 and also DAC 16 and amplifier TSBBA 17 (as shown in FIG. 4). In this configuration, a diagnostic electrode 1 made in the form of a small conductive plate is connected to a microphone input of the mobile phone headset. The recording mode is set by a driver of a respective application to the iOS or Android system. The patient's wave signal record is transmitted to the second communication device 12 connected to the analyzer 4. A multiplexer 13 may be used for communication with and analytical (diagnostic) center, as shown in FIG. 2.

Therefore, a simple diagnostic electrode may be widely distributed among the population via a trade network, pharmacies, post offices, etc. for a minor charge or even free of charge. Any person in any place may use this application to check the status of his/her health. Availability of an output audio channel in the mobile phone allows additional testing and/or compensation procedures to be used for the status correction. In this case, the testing electrode 18 is connected to the mobile phone audio output. Given similar requirements for both electrodes 1 and 18, they may be interchangeable or one electrode may be used in both modes by simply switching it over. It is also possible to use disposable electrodes. This user-specific simplification in combination with the remote automatic system provides an opportunity for a wide application of the spectral-dynamic diagnostic system and methods.

It should be also noted that a specific algorithm of the automated diagnostic system (ADS) is developed based on a set of preselected spectral-dynamic markers being highly informative with respect to an object of diagnostic for any specific disease or condition, i.e. for any nosological or functional unit. However, the method of the functional spectral-dynamic diagnostics (FSD-diagnostics) serves as a common ADS basis. On the other hand, the claimed method defines the main ADS algorithm as a sequence of operations performed in the processes of converting wave signals, comparing and recognizing relevant groups of samples, determining the degree of matching thereof subject to specific rules. Specifics of the logical and statistical processing of values of matching degrees, discrimination and logical diagnostic decision making actually define features of an object of diagnostics. Specific nosological groups of characteristic samples, weight parameters thereof or a procedure for recognition regarding the specific nosology and specific criteria values (status boundaries) defining risks and stages of progress of each specific disease are clinically determined based on special studies. In this case, specific groups of samples, weights thereof and criterion values defining the status boundaries are parametric values for each specific disease (nosology).

The hepatitis C diagnostic was chosen as an embodiment of the method for the specific nosology. As regards the chosen embodiment, in the absence of the diagnostic process automation, the FSD diagnostics technology allows a physician to distinguish four diagnosis version and four versions of a diagnostic decision respectively:

No. 1. Absence of actual individual risk of hepatitis C.

This means that as regards hepatitis C a patient is absolutely healthy.

No. 2. Presence of actual individual risk of hepatitis C.

This means that a patient is still healthy, he/she contracted a virus and at that stage the organism immune system effectively counters the hepatitis C viral infection, however, it should be noted that individual probability of developing a disease is rather high and the patient needs an individual preventive therapy.

No. 3. Signs of latent hepatitis C.

This means that the disease already began and it is either at the initial (hidden, latent) stage of progress thereof or the disease progresses in the latent (hidden, asymptomatic) form which may be proved by laboratory analysis.

No. 4. Signs of hepatitis C.

This means that the disease is at the manifested stage and the patient needs an active treatment.

The objective of the ADS is to automatically form (without involvement of a physician) these versions of diagnostic decisions.

Two databases of diagnostic reference markers (herein referred to as the "Markers") were created for the hepatitis C ADS.

Database No. 1 comprises markers: No. 1—hepatitis C, No. 2—hepatitis 2, No. 3—hepatitis C D4, No. 4—hepatitis D15, No. 5—hepeel and No. 6—Heparcomp.

Database No. 2 comprises markers: No. 1—Hepaton, No. 2—Hepabene, No. 3—Carsil, No. 4—Hepatofalk, No. 5—Flamin and No. 6—Essentiale forte.

The sequence of actions for the hepatitis C ADS is as follows:

Step 1: Checking the position and level of pathological matchings of (LPM) of the hepatitis C marker (database No. 1, marker No. 1). If this marker is in the first position on the list and the LPM thereof equals 5 or 6, then proceed to step 2. If no, than the version of a diagnostic decision is No. 1.

Step 2: Calculating the sum of the LPM markers of database No. 1. If the LPM sum exceeds 24, then proceed to step 3. If no, than the version of a diagnostic decision is No. 2.

Step 3: Calculating the sum of the LPM markers of database No. 2. If the LPM sum exceeds 18 and is less than 24, than the version of a diagnostic decision is No. 3. If the LPM sum exceeds 24, than the version of a diagnostic decision is No. 4.

The automatic diagnostics of other nosologies is also performed using respective groups of reference markers. Clinical trials of the spectral-dynamic diagnostics method demonstrated 95% diagnosing accuracy.

Therefore, diagnostic decision regarding the presence (and a stage) of a disease or absence thereof may be automatically made with high accuracy.

As a result, due to the use of the claimed method and spectral-dynamic system, selection of nosological groups of samples and weights thereof, possibility emerges to perform for the first time ever completely automatic nosological diagnostics.

Furthermore, possibility emerges to perform for the first time ever automatic online diagnostics without involvement of a physician using rather simple devices.

The above provided description of the methods and operation of the embodiments of the system illustrate but are not intended to limit possible modifications and use of alternative features.

As a result of the implementation of this invention, it is provided the on-line automatic diagnostics of a wide range of diseases. The technology and equipment proved possibilities of an extensive remote use of the system, specifically in remote areas and diagnosing diseases by the nursing personnel or even by patients themselves. In addition, this provides high diagnostic accuracy and validity.

Abbreviations (1) DE—diagnostic electrode
(2) BBA—broad-band amplifier
(3) ADC—analog-to-digital converter
(4) SDA—spectral-dynamic analyzer
(5) CR—comparator-recognizer
(6) RMBD—working marker buffer database
(7) MD—marker database
(8) MAU—matching assessment unit
(9) DMU—decision-making unit
(10) PCU—processor control unit
(11) TERM—terminal
(12) DCD—digital communication device
(13) MP—multiplexer
(14) TMD—tester marker database
(15) TSM—test signal modulator
(16) DAC—digital-to-analog converter
(17) TSBBA—testing signal broad-band amplifier
(18) TE—testing electrode

The invention claimed is:

1. A method of automatic diagnosing conditions of an object comprising:
passively receiving and recording a wave electromagnetic signal from the object's surface,
performing spectral-dynamic conversions of the signal and comparing them with ethologic samples,
processing diagnostic operations, including determining spectral-dynamic matchings of the processed signal to at least one spectral-dynamic sample from the group of samples, being a reference for the object's status to be diagnosed, and
defining a degree of matching by averaging out from degrees of matching of processed spectral-dynamic samples with each sample in a group, and
in the case when the degree of matching is below a first specified value, deciding the conclusion of absence of the status being diagnosed and displayed, and
in the case when the degree of matching is equal or is higher than the first specified value, matching the processed signal to at least one more spectral-dynamic sample, being referential to the same status, and
in the case when the degree of matching is established below a second specified value, deciding a presence of risk of an onset of the status to be diagnosed and displayed, and
in the case when the degree of matching is determined to be equal or higher than a third specified value, matching of the processed signal is performed to at least one more successive spectral-dynamic sample being referential to the same status, and
in the case when the degree of matching is determined to be below the third specified value, deciding whether the conclusion of a presence of a latent phase of the status progress is indicated, and when the degree of matching is determined to be equal to or higher than said specified value, deciding the conclusion of a presence of a manifested phase of the status to be diagnosed, and displaying it; and
performing an additional diagnostic test by forming a wave signal of a recognized sample, with this recognized sample being inverted in case it belongs to a hyperenergetic type, converting the hyperenergetic type to an analogue form, amplifying it, feeding it to a testing electrode located on the object's surface and testing an effect being produced, and then determining the relevance of the status to be diagnosed by either by the rate response time or biofeedback response time.

2. The method of claim 1, further comprising assessing the degree of matching with respect to a set of samples for a series of conditions and automatically selecting at least one sample with the highest degree of matching status, which is automatically diagnosed.

3. The method of claim 1, further comprising, for the purpose of assessing the degree of matching in addition to logical comparison procedures, using a mathematical-andstatistical procedure to assess a variance to correct the matching value for the data variability.

4. The method of claim 1, further comprising sequentially recording a set of electromagnetic wave signals, and processing the electromagnetic wave signals using spectral-dynamic analysis and the diagnostic operations, including determining the spectral-dynamic matchings of each processed signal to at least one spectral-dynamic sample being referential to the object's status to be diagnosed, averaging the obtained degrees of matching and then using the averaged degree of matching of the sample.

5. The method of claim 1, further comprising sequentially sampling, from a total duration of the record of a wave electromagnetic signal, wherein signal interval samples are processed using spectral-dynamic analysis and diagnostic operations, including determination of the spectral-dynamic matchings of each processed interval of the recorded signal to at least one spectral-dynamic sample being referential to the object's status to be diagnosed, averaging the obtained degrees of matching, and then using the averaged degree of matching.

6. The method of claim 1, comprising performing additional diagnostic testing for the group of identified samples.

7. An automatic system for diagnosing a state of an object's conditions for implementing the method as claimed in claim 1, said system comprising:
a diagnostic electrode connected in series to a broad-band amplifier, an analog-to-digital converter, a signal processing unit and a comparator for comparing with samples from a database,
characterized in that the diagnostic electrode is configured to record a wave electromagnetic signal from the object's surface, the signal processing unit is made as a spectral-dynamic analyzer, the comparator is made as a unit for recognizing images of selected samples in the spectral-dynamic representation of input signal, with a second comparator input being connected with an output of a buffer database of samples being referential to a status to be diagnosed and singled out from a common database of samples, while a positive output of the comparator is connected with a unit for assessing the degree of matching to referential samples, the output of which being connected with a decision-making unit linked with a control unit and the buffer database, and the control unit is connected with a matching degree assessment unit, a database and a control terminal for selecting the referential group of samples, controlling the process and indicating the obtained diagnosis.

8. The system of claim 7, characterized in that the diagnostic electrode, broad-band amplifier and analog-to-digital converter are connected in series and are linked to a transmission device to form a remote user terminal connected to a base spectral-dynamic analyzer via a transmission medium and a multichannel receiver-switching device.

9. The system of claim 8, comprising multiple user terminals and transmission media, including Internet, mobile, satellite and cable communication systems.

10. The system of claim 8, characterized in that a mobile phone is used as a transmission apparatus, with the diagnostic electrode being connected with a microphone input of the mobile phone, and an amplifier and a mobile phone audio channel ADC is used as an amplifier and an analog-to-digital converter of the system.

11. The system of claim 7, additionally comprising a test sample database linked to a buffer database and a modulator inverting the sample depending on its type, with the modulator control input being connected with the control unit, while the modulator output is connected in series with the digital-to-analog converter, amplifier and test electrode located on the object's surface.

* * * * *